(12) United States Patent
Zhang et al.

(10) Patent No.: US 11,737,734 B2
(45) Date of Patent: Aug. 29, 2023

(54) ULTRASOUND IMAGING DEVICE AND SYSTEM, AND IMAGE ENHANCEMENT METHOD FOR CONTRAST ENHANCED ULTRASOUND IMAGING

(71) Applicants: BEIJING SHEN MINDRAY MEDICAL ELECTRONICS TECHNOLOGY RESEARCH INSTITUTE CO., LTD., Beijing (CN); GENERAL HOSPITAL OF CHINESE PLA, Beijing (CN); SHENZHEN MINDRAY BIO-MEDICAL ELECTRONICS CO., LTD., Guangdong (CN)

(72) Inventors: Xirui Zhang, Beijing (CN); Jie Tang, Beijing (CN); Yukun Luo, Beijing (CN); Mingbo Zhang, Beijing (CN); Maodong Sang, Beijing (CN); Lanxi Xiang, Shenzhen (CN); Donghai Qin, Shenzhen (CN); Wei Fan, Shenzhen (CN)

(73) Assignees: BEIJING SHEN MINDRAY MED ELEC TECH RES INST CO LTD, Beijing (CN); GENERAL HOSPITAL OF CHINESE PLA, Beijing (CN); SHENZHEN MINDRAY BIO-MEDICAL ELECTRONICS CO., LTD., Guangdong (CN)

( * ) Notice: Subject to any disclaimer, the term of this patent is extended or adjusted under 35 U.S.C. 154(b) by 597 days.

(21) Appl. No.: 16/849,958

(22) Filed: Apr. 15, 2020

(65) Prior Publication Data
US 2020/0253586 A1    Aug. 13, 2020

Related U.S. Application Data

(63) Continuation of application No. PCT/CN2017/106391, filed on Oct. 16, 2017.

(51) Int. Cl.
A61B 8/08 (2006.01)
G06T 5/00 (2006.01)
(Continued)

(52) U.S. Cl.
CPC .............. *A61B 8/481* (2013.01); *G06T 5/007* (2013.01); *G06T 5/50* (2013.01); *G06T 7/0012* (2013.01);
(Continued)

(58) Field of Classification Search
CPC .......... A61B 8/481; G06T 5/007; G06T 5/50; G06T 7/0012
See application file for complete search history.

(56) References Cited

U.S. PATENT DOCUMENTS 6,511,426 B1 * 1/2003 Hossack ............. G01S 15/8995
600/437
7,803,115 B2 9/2010 Pan et al.
(Continued)

FOREIGN PATENT DOCUMENTS

CN    1505804 A    6/2004
CN    101017568 A    8/2007
(Continued)

OTHER PUBLICATIONS

PCT International Search Report and the Written Opinion dated Jul. 6, 2018, issued in related International Application No. PCT/CN2017/106391, with partial English translation (9 pages).
(Continued)

*Primary Examiner* — Mishawn N. Hunter
(74) *Attorney, Agent, or Firm* — SHEPPARD MULLIN RICHTER & HAMPTON LLP

(57) ABSTRACT

An ultrasound imaging device and system, and an image enhancement method for ultrasound radiography and imaging. Image enhancement coefficients of location points in a
(Continued)

examined biological tissue are computed first according to radiography channel data, and then, weighted processing is performed on the image enhancement coefficients and beam forming data.

17 Claims, 11 Drawing Sheets

(51) Int. Cl.
 *G06T 5/50* (2006.01)
 *G06T 7/00* (2017.01)
(52) U.S. Cl.
 CPC ... *A61B 8/5207* (2013.01); *G06T 2207/10132* (2013.01); *G06T 2207/20056* (2013.01)

(56) References Cited

U.S. PATENT DOCUMENTS

| | | | |
|---|---|---|---|
| 7,974,473 | B2 | 7/2011 | Nanbu |
| 11,076,834 | B2 | 8/2021 | Srinivasan et al. |
| 2005/0143655 | A1 | 6/2005 | Satoh |
| 2007/0083114 | A1* | 4/2007 | Yang .................. A61B 8/00 600/437 |
| 2007/0189635 | A1 | 8/2007 | Borsdorf et al. |
| 2009/0187106 | A1* | 7/2009 | Lee .................. G01S 15/8963 600/458 |
| 2009/0204003 | A1* | 8/2009 | Guracar .................. A61B 8/06 600/458 |
| 2012/0316439 | A1* | 12/2012 | Behar .................. A61B 5/015 600/439 |
| 2014/0185953 | A1 | 7/2014 | Hsieh et al. |
| 2014/0336513 | A1 | 11/2014 | Sang et al. |
| 2015/0015720 | A1 | 1/2015 | Kim et al. |
| 2015/0245812 | A1 | 9/2015 | Nikolov et al. |
| 2016/0012569 | A1 | 1/2016 | Hanada |
| 2017/0084024 | A1* | 3/2017 | Gurevich .................. A61B 5/7239 |
| 2017/0336500 | A1 | 11/2017 | Luo et al. |

FOREIGN PATENT DOCUMENTS

| | | |
|---|---|---|
| CN | 101159062 A | 4/2008 |
| CN | 101209211 A | 7/2008 |
| CN | 101347345 A | 1/2009 |
| CN | 101617946 A | 1/2010 |
| CN | 101645167 A | 2/2010 |
| CN | 101770639 A | 7/2010 |
| CN | 101854537 A | 10/2010 |
| CN | 101866480 A | 10/2010 |
| CN | 103126725 A | 6/2013 |
| CN | 103156636 A | 6/2013 |
| CN | 103871025 A | 6/2014 |
| CN | 104688271 A | 6/2015 |
| CN | 104720850 A | 6/2015 |
| CN | 104778662 A | 7/2015 |
| CN | 105023253 A | 11/2015 |
| CN | 105105785 A | 12/2015 |
| CN | 105147316 A | 12/2015 |
| WO | 2014045073 A1 | 3/2014 |

OTHER PUBLICATIONS

PCT International Preliminary Report on Patentability dated Apr. 30, 2020, issued in related International Application No. PCT/CN2017/106391, with English translation (10 pages).

First Search dated Jun. 13, 2022, issued in related Chinese Application No. 201780002280.1 (2 pages).

\* cited by examiner

ULTRASOUND IMAGING DEVICE AND SYSTEM, AND IMAGE ENHANCEMENT METHOD FOR CONTRAST ENHANCED ULTRASOUND IMAGING

CROSS-REFERENCE TO RELATED PATENT APPLICATION

This application is a continuation application of International Application No. PCT/CN2017/106391, filed on Oct. 16, 2017, the contents of which is incorporated herein by reference in its entirety in the present disclosure.

TECHNICAL FIELD

The present disclosure relates to an ultrasound imaging device, in particular to an image enhancement technology in contrast enhanced ultrasound imaging in the ultrasound imaging device.

BACKGROUND

In existing contrast enhanced ultrasound imaging, traditional focused transmitting is used. Taking the basic single beam as an example, only one receiving line can be formed per transmitting. Even if multi-beam processing is used, it will be still difficult to significantly reduce the number of the transmitting. For contrast enhanced ultrasound imaging, large number of transmitting mean that the intensity of the excitation to the microbubbles by the sound field in a unit frame will be increased, which will inevitably lead to a shorter duration of the contrast enhanced image, thereby affecting the integrity of blood perfusion at the lesion. The duration may be increased by reducing the number of the transmitting or decreasing the intensity of the transmitted sound field. However, it will be at the expense of image resolution and contrast signal strength.

In order to break through the above technical bottleneck, plane wave contrast enhanced imaging technology may be used. In the plane wave contrast enhanced imaging, the transmission focusing is not necessary. Therefore, the transmission sound field is more uniform, and flexible parallel multi-beam receiving may be performed. Furthermore, one frame of image can be obtained by transmitting the plan wave once. Therefore, the number of transmitting can be significantly reduced, and the frame rate can be improved. However, arc artifacts caused by signal saturation will appear in the plane wave contrast enhanced image, as shown in the white box in FIG. 1. In the process of ultrasound diagnosis, the arc artifacts will cause trouble to the doctor, making it impossible for the doctor to judge whether the strong signal is the ultrasound echoes reflected by the biological tissue or interference, which may cause the doctor to misdiagnose.

In order to eliminate the arc artifacts, on the one hand, the receiving aperture may be reduced or the receiving apodization coefficients may be adjusted, but this solution will widen the main lobe of the signal, resulting in a decrease in the lateral resolution of the imaging; on the other hand, the analog gain may be reduced so as to reduce the saturation as much as possible, but at the expense of signal strength.

SUMMARY

The present disclosure mainly provides an ultrasound imaging device and system and an image enhancement method for contrast enhanced ultrasound imaging.

In one embodiment, an image enhancement method for contrast enhanced ultrasound imaging is provided, which may include:

obtaining contrast enhanced channel data, where, an ultrasound probe is configured to transmit ultrasound waves to an examined biological tissue containing contrast agents and receive ultrasound echo signals to obtain the contrast enhanced channel data, the ultrasound echo signals received by one receiving element of the ultrasound probe form one channel data, and multiple receiving elements of the ultrasound probe are configured to receive the ultrasound echo signals to obtain multiple channel data to obtain one contrast enhanced channel data group corresponding to one location point in the biological tissue;

calculating an image enhancement coefficient at the one location point in the examined biological tissue according to the one contrast enhanced channel data group;

performing a beam-forming on the one contrast enhanced channel data group to obtain a beam-formed data at the one location point; and performing a weighting processing on the image enhancement coefficient and the beam-formed data to obtain a contrast enhanced image data corresponding to the one location point in the examined biological tissue.

In one embodiment, an image enhancement method for contrast enhanced ultrasound imaging is provided, which may include:

transmitting ultrasound waves to a region of interest containing contrast agents;

receiving echoes of the ultrasound waves to obtain echo signals;

extracting a contrast enhanced channel data according to the echo signals;

calculating an image enhancement coefficient according to the contrast enhanced channel data;

obtaining a beam-formed data according to the contrast enhanced channel data; and adjusting the beam-formed data using the image enhancement coefficient to obtain a contrast enhanced image data.

In one embodiment, an image enhancement method for contrast enhanced ultrasound imaging is provided, which may include:

transmitting ultrasound waves to a region of interest containing contrast agents;

receiving echoes of the ultrasound wave to obtain echo signals;

extracting a contrast enhanced channel data according to the echo signals;

calculating an image enhancement coefficient according to the contrast enhanced channel data;

performing a weighting processing on the calculated image enhancement coefficient and the contrast enhanced channel data to obtain a weighted channel data;

performing a beam-forming on the weighted channel data to obtain a beam-formed data;

obtaining a contrast enhanced image data according to the beam-formed data.

In one embodiment, an ultrasound imaging device is provided, which may include:

an ultrasound probe configured to transmit ultrasound waves to a region of interest containing contrast agents and receive echoes of the ultrasound waves to obtain echo signals;

a transmitting circuit configured to output an ultrasound transmitting sequence to the ultrasound probe;

an echo processing circuit configured to receive the echo signals and process the echo signals to output a channel data, wherein the echo signals received by one receiving element in the ultrasound probe form one channel data;

a processor configured to, by calling a corresponding program module, perform:

extracting a contrast enhanced channel data according to the echo signals;

calculating an image enhancement coefficient according to the contrast enhanced channel data;

obtaining a beam-formed data according to the contrast enhanced channel data; and adjusting the beam-formed data using the image enhancement coefficient to obtain a contrast enhanced image data.

In one embodiment, an ultrasound imaging system is provided, which may include:

a contrast enhanced data acquisition module configured to obtain a contrast enhanced channel data, wherein, the contrast enhanced channel data is a data for generating a contrast enhanced image extracted from a channel data of ultrasound echo signals, and the ultrasound echo signals received by each receiving element of an ultrasound probe forms one channel data;

an enhancement coefficient calculation module configured to calculate an image enhancement coefficient according to the contrast enhanced channel data;

a beam-forming module configured to perform a beam-forming on the contrast enhanced channel data to obtain a beam-formed data; and a calculation module configured to perform a weighting processing on the calculated image enhancement coefficient and beam-formed data.

In one embodiment, a computer-readable storage medium is provided, which may include a program. The program may be executed by a processor to implement the image enhancement methods above.

DETAILED DESCRIPTION

The present disclosure will be described in detail below with reference to the embodiments and drawings, where similar elements in different embodiments are designated with similar reference numbers. In the following embodiments, many details are described so as to facilitate the understanding to the present disclosure. However, those skilled in the art will easily recognize that some of the features may be omitted in different situations, or may be replaced by other elements, materials or methods. In some cases, some operations are not shown or described in the specification, which is to avoid the core part of the present disclosure being overwhelmed by too many descriptions. For those skilled in the art, detailed description of these operations is not necessary. They can fully understand these operations according to the description in the specification and general technical knowledge in the field.

In addition, the features, operations or characteristics described in the specification may be combined in any appropriate manner to form various embodiments. Furthermore, the steps or actions in the described methods may also be changed or adjusted in the order in a manner obvious to those skilled in the art. Therefore, the various orders in the description and drawings are only for clearly describing a certain embodiment, but not meant to be a necessary order unless otherwise stated that a certain order must be followed.

The serial numbers for the elements in the present disclosure, such as "first", "second", etc., are only used to distinguish the described objects, but do not have any order or technical meaning. The "connection" and "coupling" as used herein, unless otherwise specified, will include both direct and indirect connection (coupling).

Figure 1:
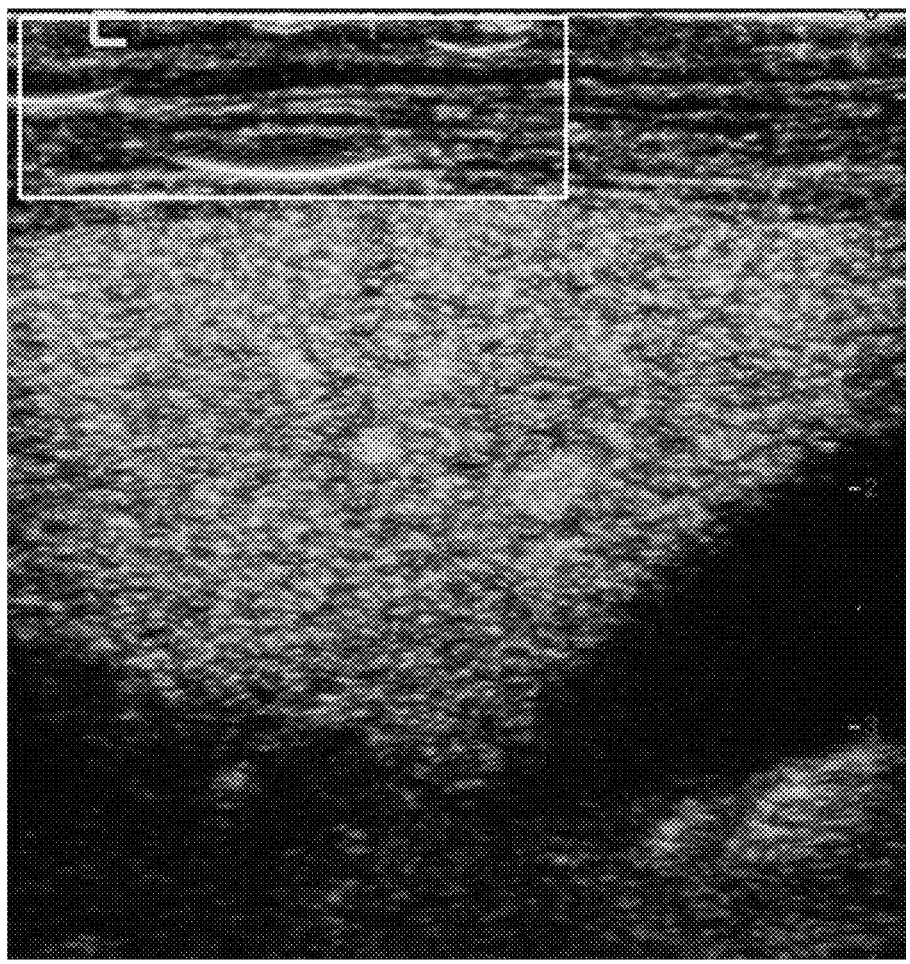
FIG. 1 is a schematic diagram of the arc artifacts in a plane wave contrast enhanced image formed by an existing ultrasound imaging device.
Figure 2:
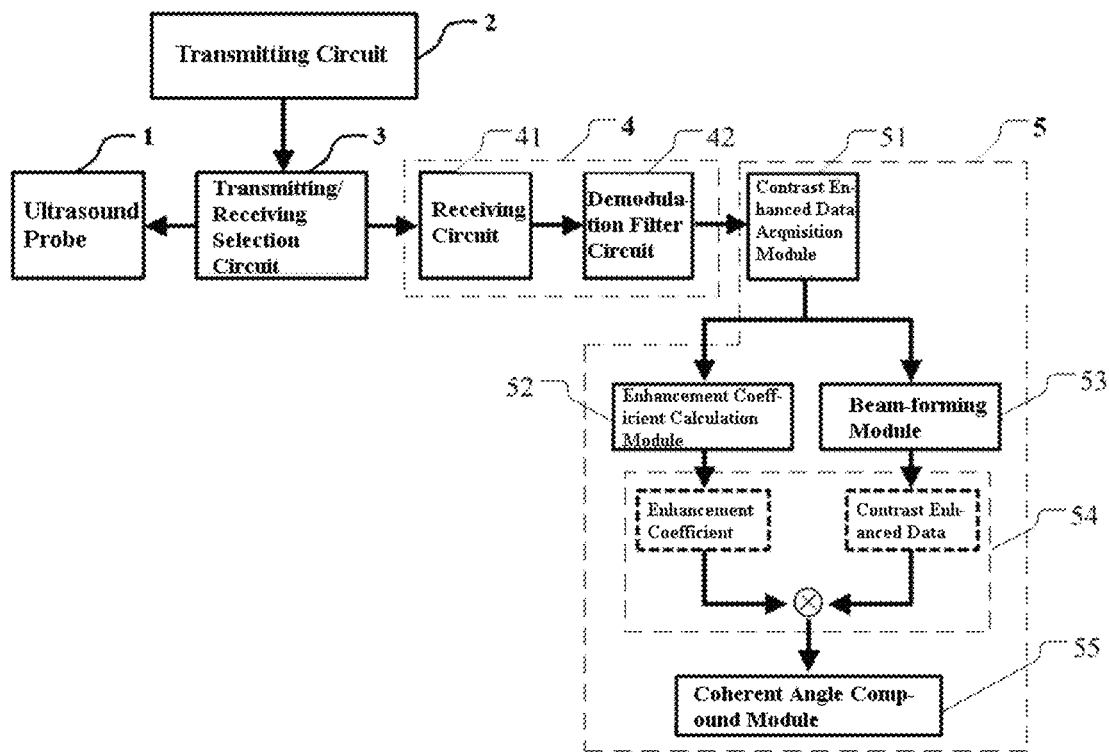
FIG. 2 is a block diagram of one embodiment of an ultrasound imaging device provided by the present disclosure.

Referring to FIG. 2, in one embodiment of the present disclosure, an ultrasound contrast enhanced imaging device may include an ultrasound probe 1, a transmitting circuit 2, a transmitting/receiving selection circuit 3, an echo processing circuit 4 and a processor 5.

The ultrasound probe 1 may be used to achieve the mutual conversion between the electric pulse signal and the ultrasound waves, so as to transmit the ultrasound waves to the biological tissue (such as the biological tissue in the human body or animal body) to be examined and receive the ultrasound echoes reflected by the tissue. In the present embodiment, the ultrasound probe 1 may include multiple elements, which are also referred to as ultrasound transducers. The multiple elements may be arranged in a row to form a linear array, or are arranged in a two-dimensional matrix to form a matrix array. The multiple elements may also form a convex array. The elements may transmit ultrasound waves according to excitation electrical signals or convert the received ultrasound waves into electrical signals. Therefore, each element may be used to transmit ultrasound waves to the biological tissues in a region of interest, and may also be used to receive ultrasound echoes returned from the tissues. When performing ultrasound examination, a transmitting sequence and a receiving sequence may be used to control which elements are used to transmit the ultrasound waves and which elements are used to receive the ultrasound waves, or control the elements to transmit ultrasound waves or receive ultrasound echoes in time-sharing. All the elements participating in the transmitting may be simultaneously excited by the electrical signals to transmit the ultrasound waves at the same time. Alternatively, the elements participating in the transmitting may be excited by the electrical signals with a certain time interval, thereby continuously transmitting the ultrasound waves with a certain time interval. If the smallest processing area from which the ultrasound waves are reflected and received in the examined biological tissue is referred to as the location point in the tissue, after the ultrasound waves reach each location point of the examined biological tissue, different reflection will occur due to the difference in tissue acoustic impedance at different location points. The reflected ultrasound waves may be picked up by the receiving elements. Each receiving element may receive the ultrasound echo signals from multiple location positions. The ultrasound echo signals from one location point received by each receiving element may form one channel data. In other words, the ultrasound echoes reflected by one location point may be picked up by multiple receiving elements, and each receiving element may output one channel data corresponding to such location point, thereby multiple receiving elements outputting multiple channel data corresponding to such location point. The multiple channel data may form a channel data group corresponding to such location point. For a receiving element, its distances to different location points in the examined biological tissue are different. Therefore, the ultrasound echoes reflected by the location points will arrive at such element at different times. The correspondence between the ultrasound echo signal and the location point may be identified according to the time when the ultrasound echoes reach the element. In some embodiments, it may also be possible that the ultrasound echoes reflected at one time point may be picked up by multiple receiving elements, and each receiving element may output one channel data corresponding to such time point, thereby multiple receiving elements outputting multiple channel data corresponding to such time point. The multiple channel data may form a channel data group corresponding to such time point.

In ultrasound imaging, one frame of two-dimensional image may be obtained by arranging multiple beam-formed data points in a two-dimensional plane according to the spatial position relationship or time sequence and perform thereon processing such as envelope detection, dynamic range compression and digital scan conversion (DSC), etc. Therefore, the location points and time points herein may not be the pixels in the two-dimensional image, but refer to the beam-formed data points. Specifically, the beam-formed data point is the result of summing the channel data after phase compensation. An important aspect of the phase compensation is to determine the times of the echoes reaching the channels, which are determined by the spatial position (the time equals to spatial distance divided by the speed of sound).

For example, after the ultrasound plane wave is transmitted once, multiple channel data groups corresponding to multiple location positions or time points may be obtained with ultrasound probe. The multiple channel data groups may be obtained by different receiving elements in time-sharing or simultaneously. After the multiple channel data groups are beam-formed, at least one frame of ultrasound contrast enhanced image may be obtained.

In the present embodiment, the ultrasound echoes may be the echoes of the ultrasound waves returned from the biological tissue containing the contrast agent being scanned by the ultrasound waves. For example, the ultrasound probe 1 may be used to transmit ultrasound waves to the biological tissue or region of interest containing the contrast agent (step 410 in FIG. 4, and step 510 in FIG. 5), and receive the echoes of the ultrasound waves to obtain the echo signals (step 420 in FIG. 4, and step 520 in FIG. 5). The contrast enhanced channel data may be obtained from the echo signals (step 430 in FIG. 4, and step 530 in FIG. 5). The ultrasound waves herein may include weakly focused ultrasound waves, plane ultrasound waves, focused ultrasound waves and so on. The region of interest may be part or entire of the biological tissue being examined.

The transmitting circuit 2 may be used to output an ultrasound transmitting sequence to the ultrasound probe 1 to control the ultrasound probe 1 to complete the single-angle or multi-angle steering transmitting of the ultrasound plane waves, and control the number of the element participating in the transmitting, and the transmitting voltage and the transmitting phase.

The transmitting/receiving selection circuit 3 may control the switching between the transmitting and receiving states of the ultrasound probe 1. In the present embodiment, the transmitting/receiving selection circuit 3 may be a selection switch. In some embodiments, if the transmitting elements and the receiving elements are unchangeable, the transmitting elements may be directly connected to the transmitting circuit 2 and the receiving elements may be directly connected to the echo processing circuit, thereby omitting the transmitting/receiving selection circuit 3.

The echo processing circuit 4 may be used to receive the ultrasound echo signals outputted from the ultrasound probe 1 and process them to output the channel data. The ultrasound echo signals received by each receiving element of the ultrasound probe 1 may form one channel data.

The processing performed by the echo processing circuit 4 on the ultrasound echo signals may include filtering, amplification, and the like. In the present embodiment, the echo processing circuit 4 may include a receiving circuit 41 and a demodulation filter circuit 42.

The receiving circuit 41 may be used to receive the ultrasound echo signals outputted from the ultrasound probe 1, and perform front-end amplification and analog-to-digital conversion (ADC) thereon to output the channel data (channel domain RF data). The front-end amplification may be implemented using one or more of a low-noise amplifier (LNA), a voltage-controlled attenuation/amplifier (VCA) and a programmable gain amplifier (PGA).

The demodulation filter circuit 42 may be used to perform quadrature demodulation on the channel data, and then perform low-pass filtering and downsampling on the base-band signal.

The processor 5 may be used to receive the channel data, and process the channel data. For example, after receiving the echo signals, the processor 5 may perform beam-forming on the echo signals, and then extract some useful signals or different component signals from the beam-formed echo signals. For example, the processor 5 may extract two different signals from the beam-formed echo signals, i.e. linear components and non-linear components. The linear components represent the anatomical characteristics of the tissue, and may subsequently be used to generate an ultrasound image of the tissue. The non-linear components represent the contrast agent microbubble information and may subsequently be used to generate a contrast enhanced image. In the present embodiment, the processor 5 may extract the linear and non-linear components from the channel data before the beam-forming to obtain contrast enhanced channel data (step 310 in FIG. 3, step 430 in FIG. 4, and step 530 in FIG. 5). Referring to FIG. 4, the processor may calculate image enhancement coefficients according to the obtained contrast enhanced channel data (step 440), and obtain beam-formed data according to the extracted contrast enhanced channel data (step 450), so as to adjust and improve the obtained beam-formed data using the calculated image enhancement coefficients to obtain contrast enhanced image data (step 460). In one embodiment, the contrast enhanced channel data group used to calculate the image enhancement coefficients and the contrast enhanced channel data group used to obtain the beam-formed data may be the same contrast enhanced channel data group. For example, the ultrasound echo signals received by one receiving element of the ultrasound probe may form one channel data, and the multiple receiving elements of the ultrasound probe may be used to respectively receive ultrasound echo signals to obtain multiple channel data which may be used to extract one contrast enhanced channel data group corresponding to one location point in the biological tissue being examined. For another example, the ultrasound echo signals received by one receiving element of the ultrasound probe may form one channel data, and the multiple receiving elements of the ultrasound probe may be used to obtain multiple channel data corresponding to one time point to obtain one contrast enhanced channel data corresponding to such time point. Improving the beam-formed data using the image enhancement coefficients can significantly improve the saturation artifacts of the contrast enhanced image and increase the contrast resolution of the images, and in particular, improve the quality of the contrast enhanced image obtained using ultrasound plane waves.

Figure 3:
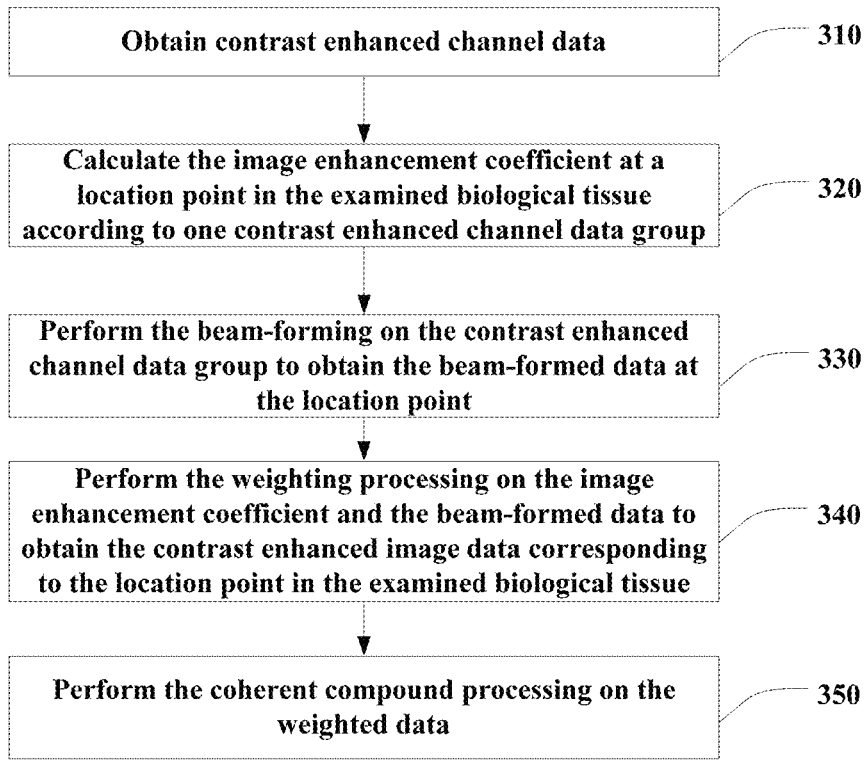
FIG. 3 is a flowchart of the image enhancement method of one embodiment.
Figure 4:
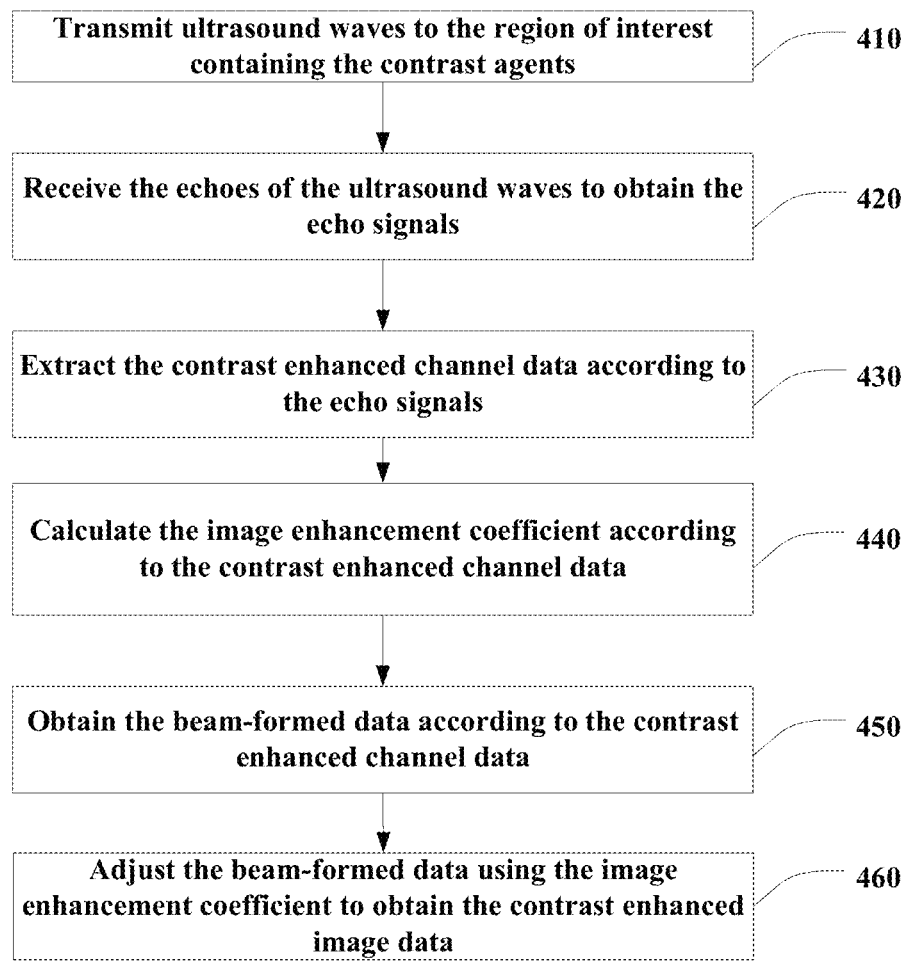
FIG. 4 is a flowchart of the image enhancement method of one embodiment.

When respectively calculating the image enhancement coefficients and the beam-formed data based on the same contrast enhanced channel data group, in one embodiment, as shown in FIG. 3, each location point in the biological tissue being examined may correspond to one contrast enhanced channel data which may be used to generate the contrast enhanced images later. The processor may calculate the image enhancement coefficients at such location point in the biological tissue according to the contrast enhanced channel data group (step 320 in FIG. 3), perform beam-forming on the contrast enhanced channel data group to obtain the beam-formed data at the such location point in the examined biological tissue (step 330 in FIG. 3), and weight the beam-formed data with the calculated image enhancement coefficients to obtain the contrast enhanced image data corresponding to such location point in the examined biological tissue (step 340 in FIG. 3). Weighting the beam-formed data with the image enhancement coefficients obtained at each location point to achieve a point-to-point weighting, the quality of the contrast enhanced image of the examined biological tissue can be increased, the saturation artifacts of the contrast enhanced image can be significantly improved, and contrast resolution of the image can be increased. Especially, the quality of the contrast enhanced images obtained using ultrasound plane waves can be increased.

Figure 6:
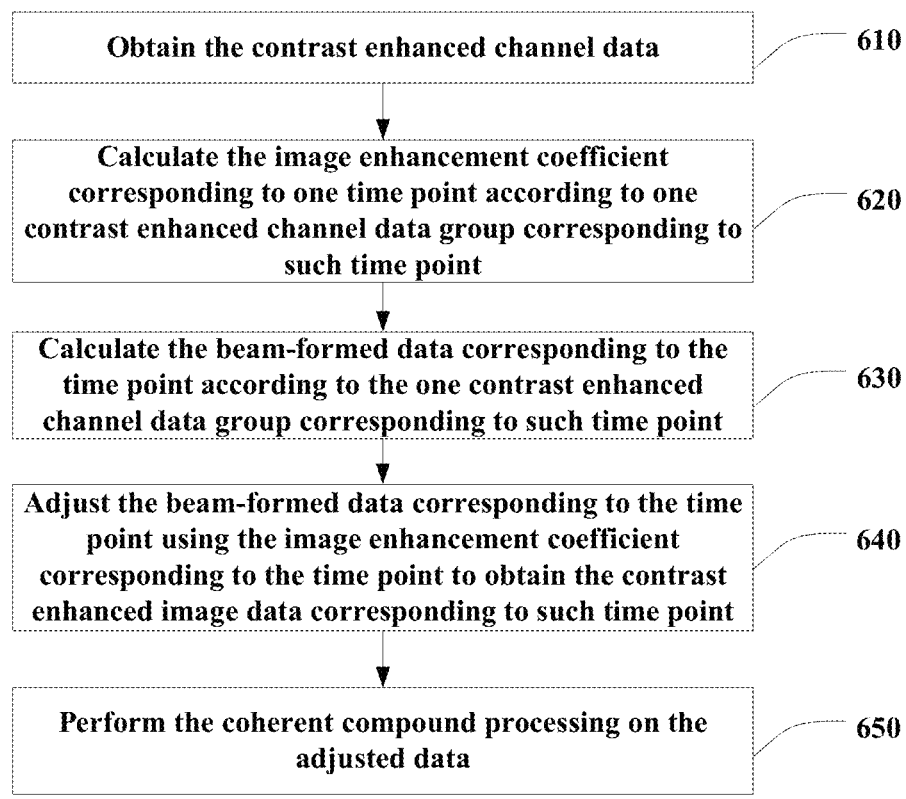
FIG. 6 is a flowchart of the image enhancement method of one embodiment.

In another embodiment, referring to FIG. 6, the contrast enhanced channel data may be obtained as the foregoing steps 510 to 530 (step 610), the image enhancement coefficient corresponding to one time point may be calculated according to one contrast enhanced channel data group corresponding to such time point (step 620), and the beam-formed data may be calculated according to the contrast enhanced channel data group corresponding to such time point (step 630). Thereafter, the beam-formed data may be adjusted using the image enhancement coefficient corresponding to such time point to obtain the contrast enhanced image data at such time point (step 640).

When adjusting the beam-formed data using the calculated image enhancement coefficients, it may be achieved by weighting the image enhancement coefficients and the beam-formed data. For example, the corresponding image enhancement coefficients and beam-formed data at the same location point may be used for the weighting process. Alternatively, the corresponding image enhancement coefficients and beam-formed data at the same time point may be used for the weighting process. The weighting process herein may be multiplying the image enhancement coefficients and beam-formed data corresponding to the same location point, or multiplying the image enhancement coefficients and beam-formed data corresponding to the same time point. In the present embodiment, it is not limited to achieve the weighting only by multiplication. Other processing methods may also be used. The point-to-point weighting processing using the image enhancement coefficients calculated according to the contrast enhanced channel data can effectively improve the contrast resolution of image and reduce the effects of the saturation artifacts.

Figure 5:
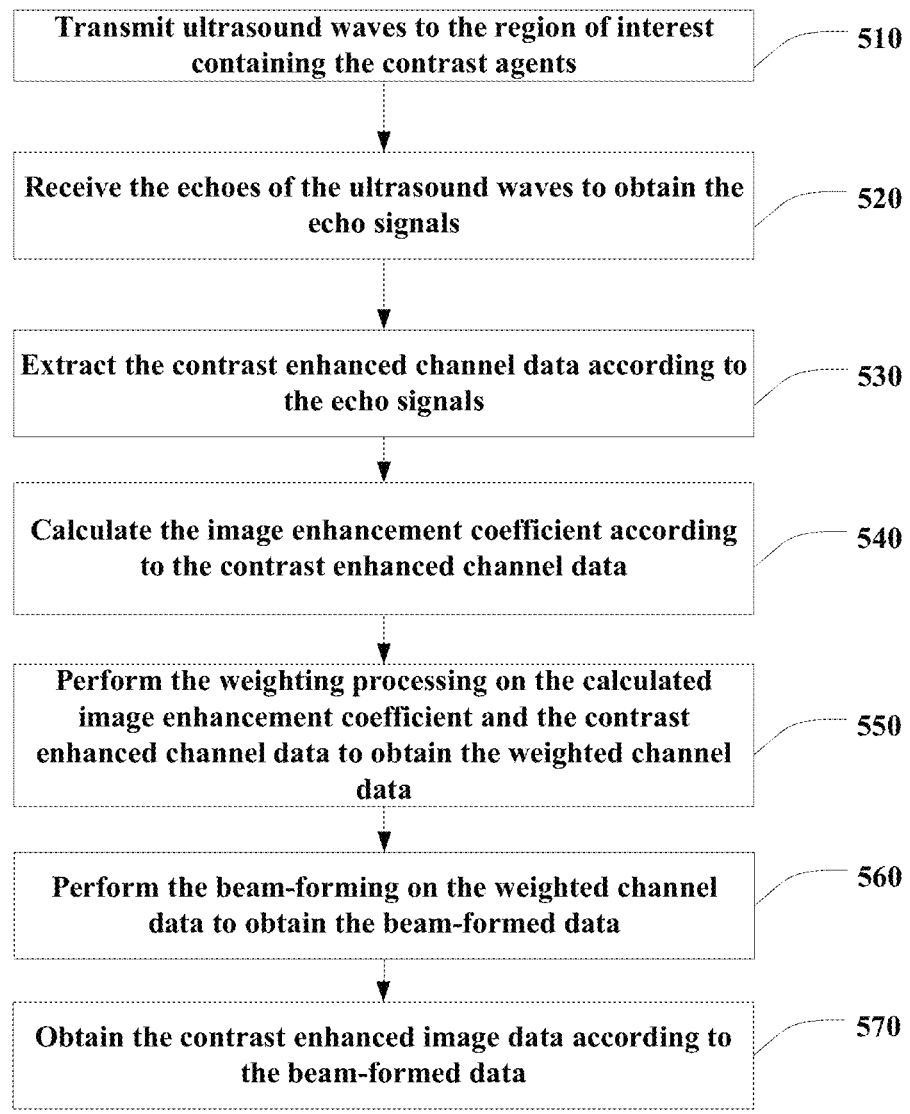
FIG. 5 is a flowchart of the image enhancement method of one embodiment.

In addition, in some embodiments, the calculated image enhancement coefficients corresponding to the location points or time points in the examined biological tissue may be weighted directly with the contrast enhanced channel data corresponding to the location points or time points by point-to-point. Thereafter, the beam-forming may be performed thereon. For example, in one embodiment, as shown in FIG. 5, the processor may extract the contrast enhanced channel data according to the echo signals received by the ultrasound probe (step 530), calculates the image enhancement coefficients according to the contrast enhanced channel data (step 540), and perform weighting processing on the calculated image enhancement coefficients and the contrast enhanced channel data to obtain the weighted channel data (step 550). Thereafter, the processor may perform the beam-forming on the weighted channel data to obtain beam-formed data (step 560), and obtain the contrast enhanced image data according to the beam-formed data (step 570). Further, the contrast enhanced channel data used to calculate the image enhancement coefficients and the contrast enhanced channel data used for the weighting processing may be the same contrast enhanced channel data group. For example, the same contrast enhanced channel data group may be the contrast enhanced channel data group corresponding to the same location point or the contrast enhanced channel data group corresponding to the same time point.

In one embodiment, the processor may calculate the image enhancement coefficients according to the contrast enhanced channel data and perform the weighting processing on the calculated image enhancement coefficients and contrast enhanced channel data to obtain the weighted channel data by:

storing one contrast enhanced channel data group, where the contrast enhanced channel data group may be one contrast enhanced channel data group corresponding to the same location point or one contrast enhanced channel data group corresponding to the same time point;

calculating the image enhancement coefficients according to this contrast enhanced channel data group; and reading the stored contrast enhanced channel data group and performing the weighting processing on the calculated image enhancement coefficients and the read contrast enhanced channel data group to obtain the weighted channel data for beam-forming.

The weighting process in the present embodiment may be multiplying the calculated image enhancement coefficients and the contrast enhanced channel data.

For each location point or time point in the examined biological tissue, the corresponding image enhancement coefficient may be calculated. For each location point or time point, the following process may be performed, that is, performing the point-to-point weighting processing on the image enhancement coefficient at such location point or time point and the contrast enhanced data at such location position or time point. The contrast enhanced data may be the contrast enhanced channel data or the beam-formed data obtained by beam-forming the contrast enhanced channel data. It can be seen that in the present embodiment the processing is performed for the noise at each location point or time point, which will not affect the overall echo processing coefficient and the overall gain. Therefore, the arc artifacts in the contrast enhanced ultrasound image can be reduced without loss of image resolution and signal strength.

The image enhancement coefficient mentioned in the present embodiment may be a correlation calculation result between the channel data corresponding to the multiple receiving elements in the contrast enhanced channel data. For example, the correlation between the channel data in the channel data group corresponding to the same location point or the same time point may be calculated, and the image enhancement coefficient may be obtained or determined according to the calculated correlation.

The correlation between the contrast enhanced channel data may specifically include the correlation between the contrast enhanced channel data in one or more dimensions of the phase domain, the space-frequency domain and the envelope domain. The phase domain may refer to the information and difference in phase between the signals of the channels (the contrast enhanced channel data). The space-frequency domain may refer to the information and differences in space and frequency between the signals of the channels (the contrast enhanced channel data). The envelope domain may refer to the information and difference in amplitude between the signals of the channels (the contrast enhanced channel data).

Specifically, the correlation between the contrast enhanced channel data in one contrast enhanced channel data group may be calculated in any one of the following way.

In the first way, the envelope detection may be performed on the contrast enhanced channel data in the one contrast enhanced channel data group to extract the envelope data, and the correlation between the contrast enhanced channel data may be calculated according to the envelope data, where the envelope detection may include the envelope detection at any power.

In the second way, the correlation may be calculated directly using the contrast enhanced channel data in one contrast enhanced channel data group. For example, the correlation may be calculated by calculating the amplitude (absolute value) or energy (square) of the sum of the contrast enhanced channel data in the one contrast enhanced channel data group.

In the third way, the phase data may be obtained by performing the phase detection on one contrast enhanced channel data group, and the correlation between the contrast enhanced channel data may be calculated according to the phase data. Specifically, phase detection may be performed on the contrast enhanced channel data to obtain the statistics in the phase data, such as the standard deviation, the variance and the distance, etc., and the correlation between the contrast enhanced channel data may be calculated according to the obtained statistics.

In the fourth way, the Fourier transform may be performed on the contrast enhanced channel data in one contrast enhanced channel data group to obtain the frequency domain data, and the correlation between the contrast enhanced channel data may be calculated according to the frequency domain data.

The image enhancement coefficient may be determined according to the correlation either directly or indirectly. In the present embodiment, the image enhancement coefficient may be obtained indirectly according to the correlation. For example, the correlation coefficient between every two channel data (such as two adjacent contrast enhanced channel data) in the one contrast enhanced channel data group may be calculated. When the correlation coefficient is less than a preset threshold, it may be determined that there is no correlation between such two channel data, otherwise it may be determined that there is correlation. The image enhancement coefficient may be obtained according to the frequency of occurrence of the no-correlation and correlation.

Specifically, let $x_1, x_2 \ldots x_N$ denote N time-delayed contrast enhanced channel data in one contrast enhanced channel data group (without any other processing except for the time delay). The image enhancement coefficient may be calculated as follows.

In step 1, the correlation coefficient $\rho$ between the two contrast enhanced channel data may be calculated according to the equation 1 below:

$$\rho_{n,n+1} = \frac{Cov(x_n, x_{n+1})}{\sqrt{Var(x_n) \cdot Var(x_{n+1})}} \quad n = 1, 2, \ldots, N-1; \quad \text{equation 1}$$

In equation 1, Cov (.) and Var (.) represent the covariance operation and the variance operation of two random variables, respectively, and n represents the $n^{th}$ contrast enhanced channel data.

In step 2, (N−1) correlation coefficients between the contrast enhanced channel data may be obtained. In step 2, an experience threshold $\beta \in (0,1)$ may be preset. When $\rho_{n,n+1} \geq \beta$, the two contrast enhanced channel data may be determined to be "correlated". When $\rho_{n,n+1} < \beta$, the two contrast enhanced channel data may be determined to be "non-correlated".

In step 3, the frequency of "correlated" and "non-correlated" between two channel data may be counted, and recorded as K1 and K2, respectively, where K1+K2=N−1. There may be two ways for calculating the enhancement coefficient: (1) the enhancement coefficient=f (K1); (2) the enhancement coefficient=1−f (K2), where f (K) may be a monotonically increasing function of the variable K and the value range is (0, 1]. This function may have various forms, as long as it meets the above requirements, and will not be described in details here.

When the ultrasound echoes come from the desired signal source (such as the tissue or the contrast agent microbubbles), the contrast enhanced channel data are relatively close in envelope, phase and frequency, etc. At this time, the correlation is high and the calculated image enhancement coefficient may tend to 1, which will retain the beam-formed data point.

When the ultrasound echoes come from random signals such as interference, clutter and noise, the contrast enhanced channel data will naturally have large differences in envelope, phase and frequency, etc., and the consistency between the contrast enhanced channel data will be low. Therefore, the calculated enhancement coefficient may tend to 0, which in turn has a suppressive effect. The final effect is to retain useful imaging content while suppressing useless side lobes and interference, etc.

It can be seen that, in one embodiment, the correlation between two adjacent contrast enhanced channel data in one contrast enhanced channel data group may be calculated, and the calculated correlation may be normalized to obtain the correlation coefficient corresponding to each contrast enhanced channel data group, thereby obtaining the image enhancement coefficient. One location point or time point may correspond to one contrast enhanced channel data group, and at least one correlation coefficient may be correspondingly obtained using one contrast enhanced channel data group.

In order to eliminate the phase difference between the contrast enhanced channel data in the contrast enhanced channel data groups, delay processing may be performed. For example, after obtaining or extracting the contrast enhanced channel data, the time delay processing may be performed on the contrast enhanced channel data. Thereafter, the time-delayed contrast enhanced channel data may be used to calculate the image enhancement coefficients and/or perform the beam-forming. For another example, the time delay processing may be performed before obtaining or extracting the contrast enhanced channel data. In one embodiment, the time delay processing may be performed on the ultrasound echo signals received by the ultrasound probe to obtain the delayed data. Thereafter, the contrast enhanced channel data representing the contrast agent information may be extracted from the delayed data, thereby eliminating the phase difference between the contrast enhanced channel data in the contrast enhanced channel data groups. Therefore, in some embodiments, the contrast enhanced channel data may be extracted according to the time-delayed echo signals. Alternatively, the contrast enhanced channel data may be time-delayed after the contrast enhanced channel data is extracted.

In some embodiments, the image enhancement method may further include performing coherent compound processing on the beam-formed data to obtain the contrast enhanced image data. By increasing the number of compound angles, the image resolution and signal-to-noise ratio can be effectively improved.

For example, referring to FIG. 3, in step 340, the weighting processing may be performed on the image enhancement coefficient and beam-formed data to obtain the weighted image data, and the coherent compound processing may be performed on the weighted image data to obtain the contrast enhanced image data (step 350). The coherent compounding may require the weighted images corresponding to multiple angles, which can be obtained specifically as follows. The ultrasound probe may be used to transmit ultrasound waves in multiple angles to the biological tissue or region of interest, and receive the echoes of the ultrasound waves to obtain echo signals. When transmitting at each angle, multiple receiving elements of the ultrasound probe may be used to receive the ultrasound echoes at such angle to obtain multiple channel data groups corresponding to such angle, thereby obtaining multiple contrast enhanced channel data groups corresponding to the multiple location positions in the examined biological tissue or the region of interest at such angle. Regarding the transmitting of the ultrasound waves in multiple angles, refer may be made to the transmitting of the ultrasound plane waves in multiple angles. For example, by controlling the excitation delay of the elements in the ultrasound probe, ultrasound plane waves in multiple steering angles may be obtained. The angle here may be measured by the angle between the direction of ultrasound transmitting and the normal of the probe. Through the methods above, multiple sets of contrast enhanced channel data groups corresponding to multiple angles may be obtained. Using the multiple contrast enhanced channel data groups corresponding to multiple location points in one angle, the image enhancement coefficients and beam-formed data corresponding to multiple location points in such angle may be respectively obtained. By performing the weighting processing on the image enhancement coefficients and the beam-formed data corresponding to the corresponding location points at one angle, the weighted image data corresponding to the corresponding location points at such angle may be obtained. Therefore, for multiple points corresponding to one angle, one weighted image data group may be respectively obtained. For the multiple angles, multiple weighted image data groups may be respectively obtained. The weighted images corresponding to the multiple angles (for example, the multiple weighted image data groups) may be subjected to the coherent compound processing at multiple angles to obtain the contrast enhanced image data. The obtained contrast enhanced image data may be a portion of one frame of contrast enhanced image data corresponding to multiple location positions, or at least one frame of contrast enhanced image data. For one angle, one location point or time point may correspond to one weighted image data.

For another example, as shown in FIG. 6, after the beam-formed data corresponding to the time point is adjusted using the image enhancement coefficient corresponding to such time point in step 640, the coherent compound processing may be performed on the adjusted data to obtain the contrast enhanced image data corresponding to such time point (step 650). The coherent compounding may require the weighted images corresponding to multiple angles, which may be obtained specifically as follows. The ultrasound probe may be used to transmit ultrasound waves to the region of interest containing the contrast agent in multiple angles. For example, the angle of the ultrasound waves may be adjusted by controlling the time delay of the transmitting elements, thereby obtaining the ultrasound waves in multiple angles.

The echoes of the ultrasound waves in the multiple angles may be received through the ultrasound probe to obtain the echo signals corresponding to the multiple angles.

The processor may extract the contrast enhanced channel data corresponding to each angle according to the echo signals corresponding to each angle. Multiple sets of contrast enhanced channel data corresponding to the multiple angles may be obtained, where one angle may correspond to one set of contrast enhanced channel data. For one angle, one contrast enhanced channel data group may be obtained for one location point or time point. Therefore, for the multiple angles, multiple sets of contrast enhanced channel data may be correspondingly obtained, respectively, which may include the multiple sets of contrast enhanced channel data corresponding to the same location point under multiple angles, where one location point under one angle may correspond to one set of contrast enhanced channel data, and one location point under multiple angles may correspond to multiple sets of contrast enhanced channel data. The contrast enhanced channel data group corresponding to one location point may include part or all of the multiple sets of contrast enhanced channel data corresponding to the same location point under multiple angles. Similarly, the one set of contrast enhanced channel data corresponding to one angle may further include the multiple contrast enhanced channel data groups corresponding to multiple location positions under such angle. In addition, the multiple sets of contrast enhanced channel data corresponding to the multiple angles may include the multiple sets of contrast enhanced channel data corresponding to the multiple angles at the same time point, where one time point under one angle may correspond to one set of contrast enhanced channel data, and one time point under multiple angles may correspond to multiple sets of contrast enhanced channel data. One contrast enhanced channel data group corresponding to one time point may include part or all of the multiple sets of contrast enhanced channel data corresponding to the same time point under multiple angles. Similarly, one set of contrast enhanced channel data corresponding to one angle may also include the multiple contrast enhanced channel data groups corresponding to multiple time points under the same angle.

According to the contrast enhanced channel data corresponding to each angle, the image enhancement coefficient and the beam-formed data corresponding to such angle may be calculated, and the beam-formed data corresponding to such angle may be adjusted using the image enhancement coefficient corresponding to such angle to obtain the adjusted data corresponding to such angle. The multiple sets of contrast enhanced channel data corresponding to the multiple angles may be used to correspondingly obtain multiple sets of adjusted data. The multiple sets of adjusted data may be subjected to the coherent compound processing according to the multiple angles to obtain the contrast enhanced image data. In some embodiments, the image enhancement coefficient and the beam-formed data corresponding to one location point or time point under each angle may be calculated according to the set of contrast enhanced channel data corresponding to the same location point or time point under such angle. Thereafter, the beam-formed data corresponding to the location point or time point under each angle may be adjusted using the image enhancement coefficient corresponding to the same location point or time point under such angle, thereby obtaining the adjusted data corresponding to the location point or time point under each angle. The following method may also be used. The image enhancement coefficients and the beam-formed data corresponding to multiple location points or time points under one angle may be obtained using the multiple contrast enhanced channel data groups corresponding to the multiple location points or time points under such angle. By performing the weighting processing on the image enhancement coefficients and the beam-formed data corresponding to the corresponding location point or time point under one angle, one weighted image data corresponding to the corresponding location point or time point under the corresponding angle. One weighted image data group may be obtained for the multiple location points or time points under one angle, and therefore multiple weighted image data groups may be obtained for the multiple angles. The multiple weighted image data groups may be subjected to the coherent compound processing according to the multiple angles to obtain the contrast enhanced image data. The obtained contrast enhanced image data may be a portion of one frame of contrast enhanced image data corresponding to the multiple location points or time points, or at least one frame of contrast enhanced image data.

The adjustment herein may be a weighting processing. For details, please refer to the previous description. Using the multiple sets of contrast enhanced channel data corresponding to one location point or time point under multiple angles, multiple sets of adjusted data may be obtained accordingly. The multiple sets of adjusted data may be subjected to the coherent compound processing according to the multiple angles to obtain the contrast enhanced image data.

In the embodiment shown in FIG. 5, the coherent compound processing may be performed after the beam-forming. For example, in one embodiment, the ultrasound probe may be used to transmit ultrasound waves in multiple angles to the region of interest containing the contrast agent, and receive the echoes of the ultrasound waves in the multiple angles to obtain the echo signals corresponding to the multiple angles. The processor may extract the contrast enhanced channel data corresponding to each angle according to the echo signals corresponding to each angle. Multiple sets of contrast enhanced channel data may be accordingly obtained for the multiple angles. For the detailed description of multiple sets of contrast enhanced channel data, reference may be made to the related description above, which will not be described here again.

According to the contrast enhanced channel data corresponding to each angle, the image enhancement coefficient corresponding to each angle may be calculated. The weighting processing may be performed on the image enhancement coefficient corresponding to each angle and the contrast enhanced channel data corresponding to such angle to obtain the weighted channel data corresponding to each angle. The beam-forming may be performed on the weighted channel data to obtain the beam-formed data corresponding to each angle, thereby obtaining the beam-formed data corresponding to the multiple angles. Thereafter, the coherent compound processing may be performed on the beam-formed data corresponding to the multiple angles to obtain the contrast enhanced image. In some embodiments, the image enhancement coefficient corresponding to one location point or time point under each angle may be calculated according to one set of contrast enhanced channel data corresponding to the same location point or time point under such angle. Thereafter, the weighting processing may be performed on the image enhancement coefficient corresponding to the location point or time point under each angle and the contrast enhanced channel data corresponding to the same location point or time point under such angle to obtain the weighted channel data corresponding to the location point or time point under each angle, thereby obtaining the weighted channel data corresponding to the location point or time point under the multiple angles. The beam-forming may be performed on the weighted channel data corresponding to the location point or time point under the multiple angles to obtain the beam-formed data corresponding to the same location point or time point under the multiple angles. Thereafter, the coherent compound processing may be performed on the beam-formed data corresponding to the location point or time point under the multiple angles to obtain the contrast enhanced image data. In other embodiments, the image enhancement coefficients corresponding to multiple time points or location points under one angle may be obtained using the multiple contrast enhanced channel data groups corresponding to the multiple time points or location points under such angle. Thereafter, the weighting processing may be performed on the image enhancement coefficients corresponding to the corresponding location point or corresponding time point under each angle and the contrast enhanced channel data corresponding to the corresponding location point or corresponding time point under such angle to obtain one weighted image data corresponding to the corresponding location point or corresponding time point under each angle. Therefore, one weighted channel data group may be obtained for the multiple location points or the multiple time points under one angle, thereby correspondingly obtaining multiple weighted channel data groups for the multiple location points or the multiple time points under the multiple angles. The beam-forming may be respectively performed on the multiple weighted channel data groups to obtain one beam-formed data group corresponding to the multiple time points or the location points under one corresponding angle, thereby obtaining multiple beam-formed data groups corresponding to the multiple time points or location points under the multiple angles. Finally, the coherent compound processing may be performed on the multiple beam-formed data groups according to the multiple angles to obtain the contrast enhanced image data. The obtained contrast enhanced image data may be part of one frame of contrast enhanced image data corresponding to the multiple time points or location points, or at least one frame of contrast enhanced image data.

In the case of multiple angles, for the contrast enhanced channel data corresponding to each angle, the image enhancement coefficient may be obtained by calculating the correlation between the contrast enhanced channel data in one set of contrast enhanced channel data corresponding to the same location point or time point at one angle. Regarding how to perform the correlation calculation using the contrast enhanced channel data, reference may be made to the previous description.

Referring to FIG. 2, in some embodiments, an ultrasound system may include an ultrasound probe 1, a transmitting circuit 2, a transmitting/receiving selection circuit 3, an echo processing circuit 4 and a processor 5. The ultrasound probe may be used to transmit ultrasound waves to the region of interest containing the contrast agent, and receive the echoes of the ultrasound waves to obtain echo signals. The transmitting circuit may be used to output the ultrasound transmitting sequence to the ultrasound probe. The echo processing circuit may be used to receive and process the echo signals to output the channel data. The echo signals received by each receiving element in the ultrasound probe may form one channel data. The processor may execute the following steps by calling the corresponding program module:

extracting the contrast enhanced channel data according to the echo signals;

calculating the image enhancement coefficient according to the contrast enhanced channel data;

obtaining the beam-formed data according to the contrast enhanced channel data; and adjusting the beam-formed data using the image enhancement coefficient to obtain the contrast enhanced image data.

Regarding these steps executed by the processor, reference may be made to the related descriptions about the step 410 to step 460 in FIG. 4 above, which will not be described here again.

In some embodiments, the one contrast enhanced channel data group used to calculate the image enhancement coefficient and the one contrast enhanced channel data group used to calculate the beam-formed data may be the same contrast enhanced channel data group.

In some embodiments, the contrast enhanced channel data may be one contrast enhanced channel data group corresponding to the same location point, or one contrast enhanced channel data group corresponding to the same time point.

In some embodiments, the image enhancement coefficient may be obtained by calculating the correlation between the contrast enhanced channel data in one contrast enhanced channel data group corresponding to the same location point or the same time point.

In some embodiments, the processor may calculate the image enhancement coefficient according to the contrast enhanced channel data, obtain the beam-formed data according to the contrast enhanced channel data and adjust the beam-formed data using the image enhancement coefficient by one of the following ways.

In the first way, the image enhancement coefficient at one location point in the examined biological tissue may be calculated according to one contrast enhanced channel data group, the beam-forming may be performed on the one contrast enhanced channel data group to obtain the beam-formed data at the location point, and the weighting processing may be performed on the image enhancement coefficient and the beam-formed data to obtain the contrast enhanced image data corresponding to such location point in the examined biological tissue. The one contrast enhanced channel data group may be the multiple contrast enhanced channel data corresponding to the one location point in the region of interest received by the multiple receiving elements of the ultrasound probe.

In the second way, the image enhancement coefficient corresponding to one time point may be calculated according to one contrast enhanced channel data group corresponding to such time point, the beam-formed data corresponding to such time point may be calculated according to the one contrast enhanced channel data group corresponding to such time point, and, the weighting processing may be performed on the image enhancement coefficient corresponding to such time point and the beam-formed data corresponding to the such time point to obtain the contrast enhanced image data at such time point.

Regarding the first way, reference may be made to the previous related description about the steps in the embodiment shown in FIG. 3. Regarding the second way, reference may be made to the previous related description about the steps in the embodiment shown in FIG. 6.

In some embodiments, the contrast enhanced channel data may be extracted according to the time-delayed echo signals. Alternatively, after the contrast enhanced channel data is extracted, the time-delay processing may be performed on the contrast enhanced channel data. Regarding the time delay, reference may be made to the relevant description above.

In some embodiments, the ultrasound probe may be used to transmit ultrasound waves in multiple angles to the region of interest containing the contrast agent, and receive the echoes of the ultrasound waves in the multiple angles to obtain the echo signals corresponding to the multiple angles. The processor may extract the contrast enhanced channel data corresponding to each angle according to the echo signals corresponding to such angle, calculate the image enhancement coefficient and beam-formed data corresponding to each angle according to the contrast enhanced channel data corresponding to such angle, and perform the weighting processing on the image enhancement coefficient corresponding to each angle and the beam-formed data corresponding to such angle to obtain the weighted channel data corresponding to such angle, thereby obtaining the weighted channel data corresponding to the multiple angles. The processor may perform the coherent compound processing on the weighted channel data corresponding to the multiple angles to obtain the contrast enhanced image. In some embodiments, the obtained multiple sets of contrast enhanced channel data corresponding to the multiple angles may include the multiple sets of contrast enhanced channel data corresponding to the same time point or location point under the multiple angles, where one time point or location point under one angle may correspond to one set of contrast enhanced channel data. Regarding the multi-angle coherent compound processing, reference may be made to the specific description about steps 350 and 650 above, especially about how to perform the multi-angle transmitting and how to perform the coherent compound processing on the contrast enhanced channel data corresponding to the multiple angles.

In some embodiments, the program module executed by the processor may form an ultrasound imaging system, which may include a contrast enhanced data acquisition module 51, an enhancement coefficient calculation module 52, a beam-forming module 53 and a calculation module 54. In addition, the system may further include a coherent angle compound module 55.

The contrast enhanced data acquisition module 51 may be used to obtain the contrast enhanced channel data. The contrast enhanced channel data may be the data for generating the contrast enhanced image extracted from the channel data of the ultrasound echo signals. The ultrasound echo signals received by each receiving element of the ultrasound probe may form one channel data. For example, one contrast enhanced channel data group may be correspondingly obtained at each location point or each time point in the region of interest.

The enhancement coefficient calculation module 52 may be used to calculate the image enhancement coefficient according to the contrast enhanced channel data, such as calculate the image enhancement coefficient at one location point or one time point according to the contrast enhanced channel data. Specifically, the enhancement coefficient calculation module 52 may calculate the correlation between the contrast enhanced channel data in each contrast enhanced channel data group, and determine the image enhancement coefficient at the location point in the examined biological tissue corresponding to such contrast enhanced channel data according to the correlation.

The beam-forming module 53 may be used to perform beam-forming on the contrast enhanced channel data to obtain the beam-formed data. For example, according to the contrast enhanced channel data corresponding to the same location point or the same time point, the beam-formed data corresponding to such location point or time point may be obtained.

The calculation module 54 may be used to perform the weighting processing on the calculated image enhancement coefficients and the beam-formed data, such as perform the weighting processing on the image enhancement coefficient corresponding to the same location point or time point and the beam-formed data corresponding to such location point or time point. By determining the image enhancement coefficient according to the correlation between the contrast enhanced channel data and applying it to the plane wave beam-formed data, the weight of the beam-formed data corresponding to the signal saturation can be effectively reduced, and the side lobes can be reduced, thereby suppressing the off-axis interference and clutter. Therefore, the artifacts can be eliminated and the contrast resolution can be increased.

The contrast enhanced data acquisition module 51 in the present embodiment may be used to perform step 310, step 430, step 530 or step 610 in FIG. 3 to FIG. 6. The enhancement coefficient calculation module 52 may be used to perform step 440, step 540, step 620 or step 320 in FIG. 3 to FIG. 6. The beam-forming module 53 may be used to perform step 330, step 450, step 560 or step 630 in FIG. 3 to FIG. 6. The calculation module 54 may be used to perform step 340, step 460, step 550 or step 640 in FIG. 3 to FIG. 6. Therefore, reference may be made to the detailed explanation of the relevant steps above, which will not be described here again.

In some embodiments, the ultrasound imaging system may further include a time delay processing module which may be used to phase align the multiple channel data at each location point or time point. For one location point, the ultrasound echoes reflected by such location point may be picked up by multiple receiving elements to form one channel data corresponding to such location point. However, since the distances between the location point and the multiple receiving elements are different, the phases of the ultrasound echo signals outputted by different receiving elements are different. After being processed by the time delay processing module, the phase of the channel data corresponding to such location point may be consistent. In one embodiment, after the contrast enhanced data acquisition module 51 extracts the contrast enhanced channel data representing the contrast agent information from the channel data, the time delay processing module may perform the time delay processing on the contrast enhanced channel data so as to eliminate the phase differences between the contrast enhanced channel data. In another embodiment, the delay processing module may perform the delay processing on the channel data before extracting the contrast enhanced channel data representing the contrast agent information from the channel data. The contrast enhanced channel data processed in the enhancement coefficient calculation module 52 and the beam-formed module 53 may be the time-delayed contrast enhanced channel data.

The beam-forming module 53 may be specifically configured to perform processing such as dynamic receiving aperture, apodization and phase rotation, etc. on the contrast enhanced channel data outputted by the contrast enhanced data acquisition module 51, and perform channel summation processing thereon.

The calculation module 54 may perform the point-to-point weighting processing on the image enhancement coefficients and the beam-formed data by: multiplying the image enhancement coefficients corresponding to the location points or time points in the region of interest by the beam-formed data corresponding to the corresponding location points or time points to obtain the contrast enhanced data for subsequent imaging. For a certain receiving element, the distances to different location points in the examined biological tissue are different. Therefore, the times when the ultrasound echoes reflected by the location points arrive at such element will be different. The correspondence between the ultrasound echo signals and the location points may be identified according to the time when the ultrasound echoes arrive at such element. Therefore, the image enhancement coefficients and the beam-formed data respectively obtained according to the contrast enhanced channel data at the location points to be imaged in the examined biological tissue may be in a one-to-one correspondence relationship. The data obtained by multiplying these two are then used to obtain the contrast enhanced image. This way, the plane wave contrast enhanced image in which the arc artifacts are reduced or even eliminated may be obtained. Since the image enhancement coefficients are multiplied with the corresponding beam-formed data, but not with the image pixels, it may be a screening processing on the data for the contrast enhanced ultrasound imaging, which can effectively suppress the random signals such as interference, clutter and noise, etc. in the echo signals and enhance the contrast resolution of contrast enhanced image.

The coherent angle compound module 55 may be used to perform the coherent compounding (before the envelope detection) on the enhanced beam-formed data in all transmitting angles so as to mainly increase the SNR (signal to noise ratio) and the lateral resolution of the image. Specifically, the ultrasound probe 1 may transmit ultrasound plane waves in different angles to excite the medium. The coherent angle compound module 55 may perform the beam-forming processing on the echo data in each angle, and perform weighted summation on the beam-formed data in all angles. In some examples, the contrast enhanced data acquisition module may extract the contrast enhanced channel data corresponding to each angle according to the echo signals corresponding to such angle, thereby obtaining the multiple sets of contrast enhanced channel data corresponding to the multiple angles. The enhancement coefficient calculation module may calculate the image enhancement coefficient corresponding to each angle according to the contrast enhanced channel data corresponding to such angle. The beam-forming module may calculate the beam-formed data corresponding to each angle. The calculation module may perform the weighting processing on the image enhancement coefficient corresponding to each angle and the beam-formed data corresponding to such angle to obtain the weighted channel data corresponding to such angle, so as to obtain the weighted channel data corresponding to the multiple angles. The coherent angle compound module 55 may perform the coherent compound processing on the weighted channel data corresponding to the multiple angles to obtain the contrast enhanced image data.

Therefore, in the present embodiment, the contrast enhanced channel data may be used, together with the beam-forming processing. First, the contrast enhanced channel data may be subjected delay, dynamic receiving aperture and apodization weighting processing. Thereafter, the information in the phase domain, envelope domain or frequency domain, etc. of the contrast enhanced channel data after the processing above may be extracted to calculate the image enhancement coefficient in the plane wave contrast enhanced imaging. Finally, this set of coefficients may be applied to the plane wave beam-formed data. This way, the saturation artifacts in the plane wave contrast enhanced image can be significantly improved and the contrast resolution of the image can be increased.

In the embodiments above, the contrast enhanced data acquisition module 51, the enhancement coefficient calculation module 52, the beam-forming module 53, the calculation module 54, the coherence angle compound module 55 and the time delay processing module may all be functions or program modules of the processor. In some embodiments, the contrast enhanced data acquisition module 51, the enhancement coefficient calculation module 52, the beam-forming module 53, the calculation module 54, the coherence angle compound module 55 and the time delay processing module may be implemented by one or more processors, and the processor may be a processor provided in the host, or a processor separate from the host of the ultrasound device, such as a processor in a server or a portable device, as long as the above-mentioned functions can be implemented.

In the present embodiment, a linear probe of an ultrasound platform is used to acquire the plane wave contrast enhanced baseband channel data of the dog liver (of course, this embodiment may also be applied to radio frequency channel data) which include a total of 211 frames, and the image enhancement methods proposed by the present embodiment are simulated and verified based on the MATLAB simulation platform. FIG. 7 to FIG. 12 show the typical comparison results of three frames.

Figure 7:
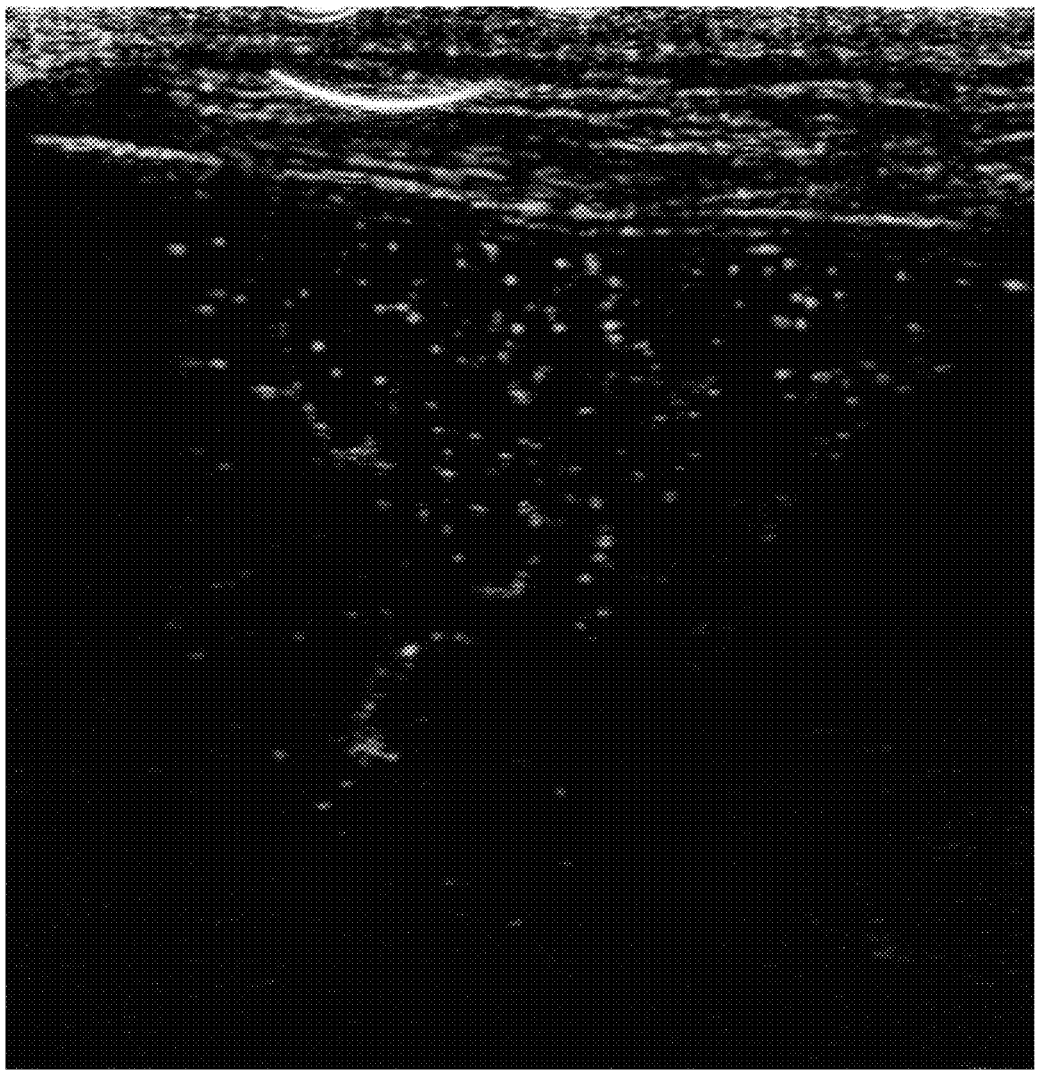
FIG. 7 is a plane wave contrast enhanced image in the early stage of perfusion using the existing solutions.
Figure 8:
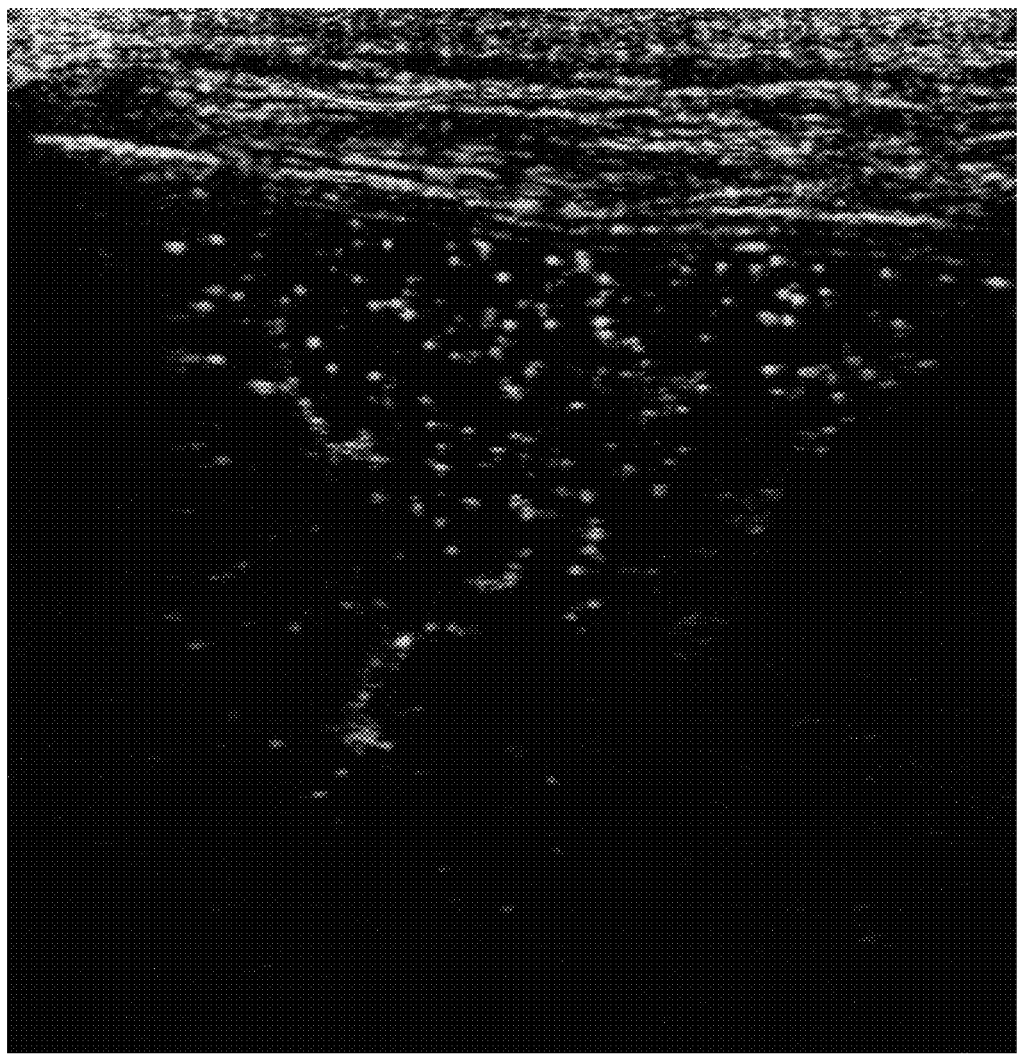
FIG. 8 is a plane wave contrast enhanced image in the early stage of perfusion formed by the ultrasound imaging device provided by the present disclosure.
Figure 9:
FIG. 9 is a plane wave contrast enhanced image using the existing solutions in the arterial phase.
Figure 10:
FIG. 10 is a plane wave contrast enhanced image in the arterial phase formed by the ultrasound imaging device provided by the present disclosure.
Figure 11:
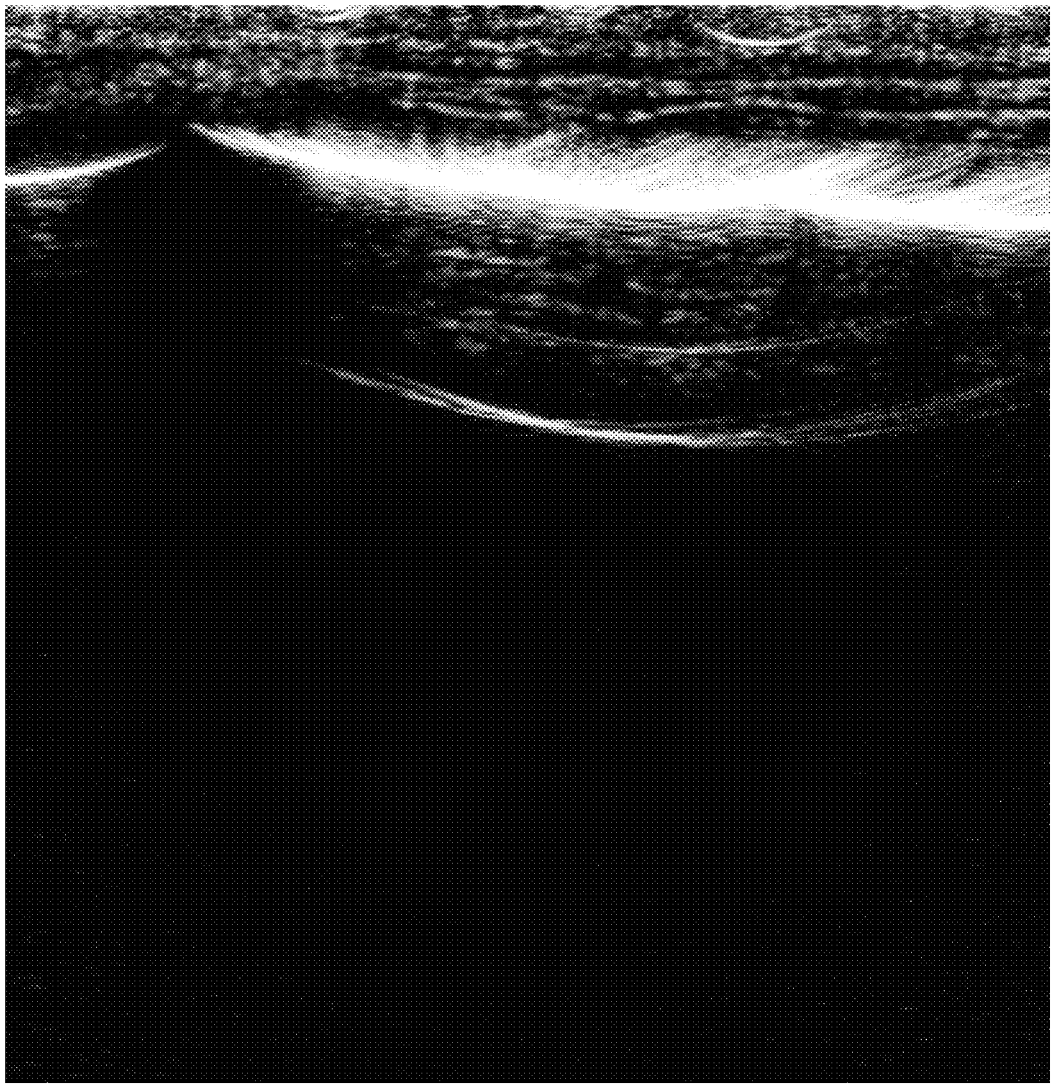
FIG. 11 is a schematic diagram of extreme saturation artifacts appearing in a plane wave contrast enhanced image obtained by the existing solutions.
Figure 12:
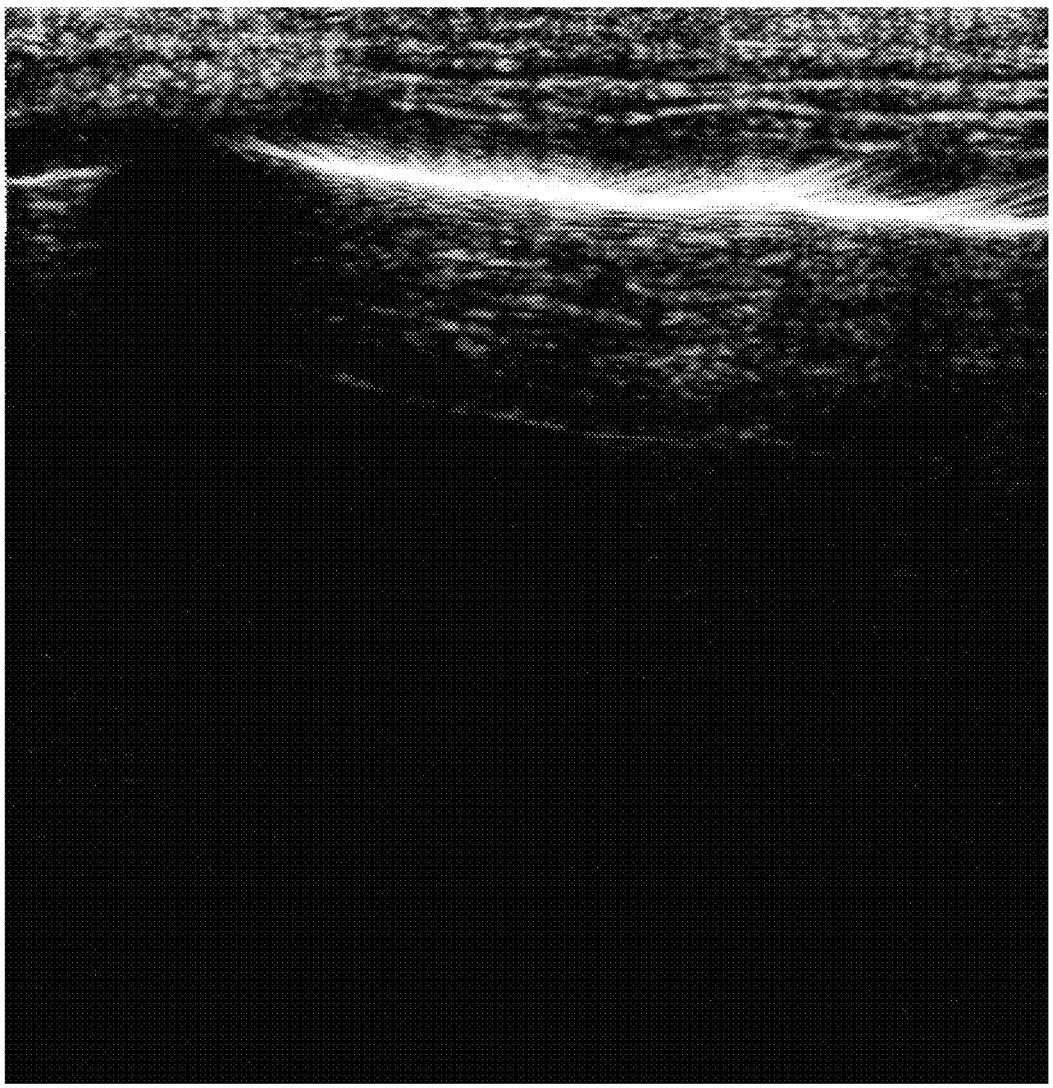
FIG. 12 is a schematic diagram of extreme saturation artifacts appearing in a plane wave contrast enhanced image formed by the ultrasound imaging device provided by the present disclosure.

As shown in FIG. 7 to FIG. 12, by the image enhancement methods proposed in the present embodiment, the saturation artifacts in the mid and near fields are significantly improved, or even completely eliminated. It may also be found through the comparison between FIG. 9 and FIG. 10 that, with equivalent noise, the microbubble signals in the plane wave contrast enhanced image to which the enhancement method is used are fuller. FIG. 7 is a plane wave contrast enhanced image in the early stage of perfusion using the existing solutions, and FIG. 8 is a plane wave contrast enhanced image in the early stage of perfusion formed by the image enhancement method provided by the present embodiment. It can be seen from these figures that the saturation artifacts in the middle and near fields has been greatly improved through the use of the enhancement method, and even eliminated completely. Similarly, FIG. 11 is a schematic diagram of the extreme saturation artifacts appearing in the plane wave contrast enhanced image using the existing solutions, and FIG. 12 is a schematic diagram of the extreme saturation artifacts appearing in the plane wave contrast enhanced image formed by the ultrasound imaging device provided in the present embodiment. Similarly, it can be seen from these figures that the saturation artifacts in the middle and near fields has been greatly improved, and even eliminated completely, and the quality of the image is increased.

Therefore, the image enhancement methods for the contrast enhanced ultrasound imaging proposed in the present disclosure have great clinical value. The embodiments will not be limited to the plane wave contrast enhanced imaging, but be also applicable to traditional focused wave contrast enhanced imaging.

The principles, characteristics and details of the image enhancement methods have been described in detail in the embodiments of the ultrasound imaging device above, and will not be described here again.

A person skilled in the art may understand that all or part of the functions of the various methods in the embodiments above may be implemented by hardware, or by a computer program. When all or part of the functions in the embodiments above are implemented by a computer program, the program may be stored in a computer-readable storage medium. The storage medium may include a read-only memory, a random access memory, a magnetic disk, an optical disk, a hard disk or the like. The program may be executed by a computer to implement the functions above. For example, the program may be stored in the memory of the device. When the processor executes the program in the memory, all or part of the functions above may be implemented. In addition, when all or part of the functions in the embodiments above are implemented by a computer program, the program may also be stored in a storage medium such as a server, another computer, a magnetic disk, an optical disk, a flash disk, or a mobile hard disk, etc., and may be saved to the memory of the local device by download or copy or used to update the system of the local device. When the program in the memory is executed by the processor, all or part of the functions in the embodiments above may be implemented. Therefore, in some examples, a computer-readable storage medium may include a program which may be executed by a processor to implement the image enhancement methods above.

In the ultrasound imaging devices and the image enhancement methods of the contrast enhanced ultrasound imaging thereof according to the embodiments above, the image enhancement coefficients at the location point in the examined biological tissue may be calculated according to the contrast enhanced channel data. Thereafter, the point-to-point weighting processing may be performed on the image enhancement coefficients and the beam-formed data. Therefore, the arc artifacts in the contrast enhanced ultrasound image can be reduced without losing image resolution and signal strength.

The present disclosure have been described through specific examples, which are only used to facilitate the understanding to, but not intended to limit, the present disclosure. For those ordinarily skilled in the art, based on the concepts of the present disclosure, changes to the specific embodiments above may be made.

The invention claimed is:

1. An image enhancement method for contrast enhanced ultrasound imaging, comprising:
   obtaining contrast-enhanced channel data, wherein, an ultrasound probe is configured to transmit ultrasound waves to an examined biological tissue containing contrast agents and receive ultrasound echo signals to obtain the contrast-enhanced channel data, each receiving element of multiple receiving elements of the ultrasound probe is configured to receive the ultrasound echo signals to obtain a piece of the contrast-enhanced channel data, the multiple receiving elements of the ultrasound probe are configured to receive the ultrasound echo signals to obtain multiple pieces of the contrast-enhanced channel data, and the contrast-enhanced channel data corresponding to one location point in the biological tissue;
   calculating an image enhancement coefficient at the one location point in the examined biological tissue according to the contrast-enhanced channel data, the image enhancement coefficient being indicative of correlations among the multiple pieces of the contrast-enhanced channel data corresponding to the multiple receiving elements;
   performing a beam-forming on the contrast-enhanced channel to obtain a beam-formed data at the one location point; and
   performing weighting processing on the image enhancement coefficient and the beam-formed data to obtain contrast-enhanced image data corresponding to the one location point in the examined biological tissue.

2. The method of claim 1, wherein calculating the image enhancement coefficient at the one location point in the examined biological tissue according to the contrast-enhanced channel data comprises:
   calculating a correlation between each piece of the contrast-enhanced channel data, and determining the image enhancement coefficient according to the correlations.

3. The method of claim 2, wherein calculating the correlation between each piece of the contrast-enhanced channel data comprises:
   performing an envelope detection on each piece of the contrast-enhanced channel data to obtain envelope data, and calculating the correlation between each piece of the contrast-enhanced channel data according to the envelope data, wherein the envelope detection comprises an envelope detection at a power; or
   calculating the correlation between each piece of the contrast-enhanced channel data directly using the contrast-enhanced channel data; or
   performing a phase detection on each piece of the contrast-enhanced channel data to obtain phase data, and calculating the correlation between each piece of the contrast-enhanced channel data according to the phase data; or
   performing a Fourier transform on each piece of the contrast-enhanced channel data to obtain frequency domain data, and calculating the correlation between each piece of the contrast-enhanced channel data according to the frequency domain data.

4. The method of claim 1, wherein performing the weighting processing on the image enhancement coefficient and the beam-formed data comprises: multiplying the image enhancement coefficient and the beam-formed data corresponding to the one location point.

5. The method of claim 1, further comprising: after obtaining the contrast-enhanced channel data, performing time delay processing on the contrast-enhanced channel data.

6. The method of claim 1, further comprising: before obtaining the contrast-enhanced channel data:
   performing time delay processing on the ultrasound echo signals to obtain time-delayed data; and
   extracting contrast-enhanced channel data representing contrast agent information from the time-delayed data.

7. The method of claim 1, wherein performing the weighting processing on the image enhancement coefficient and the beam-formed data to obtain the contrast-enhanced image data corresponding to the one location point in the examined biological tissue comprises:
   performing the weighting processing on the image enhancement coefficient and the beam-formed data to obtain weighted image data comprising multiple weighted images respectively corresponding to multiple angles of using the ultrasound probe; and
   performing coherent compound processing on the multiple weighted images to obtain the contrast-enhanced image data by compounding the multiple weighted images.

8. The method of claim 7, wherein,
   obtaining the contrast-enhanced channel data using the ultrasound probe comprises:
      obtaining contrast-enhanced channel data corresponding to the multiple angles of using the ultrasound probe, wherein, the contrast-enhanced channel data corresponding to the multiple angles are derived from ultrasound echo signals of the ultrasound waves transmitted to the examined biological tissue by the ultrasound probe in the multiple angles, and, when transmitting in each angle of the multiple angles, the multiple receiving elements of the ultrasound probe are configured to receive the ultrasound echo signals corresponding to an angle of the multiple angles to obtain multiple pieces of the contrast-enhanced channel data corresponding to the one location point in the examined biological tissue in the angle; and
   performing the weighting processing on the image enhancement coefficient and the beam-formed data to obtain the weighted image data and performing the coherent compound processing on the multiple weighted images to obtain the contrast-enhanced image data comprises:
      obtaining the image enhancement coefficient and the beam-formed data corresponding to the one location point in the angle according to the contrast-enhanced channel data corresponding to the one location point in the angle, performing the weighting processing on the image enhancement coefficient and the beam-formed data corresponding to the one location point in the angle to obtain a weighted image corresponding to the one location point in the angle, obtaining the multiple weighted images corresponding to the multiple angles, and performing the coherent compound processing on the multiple image data corresponding to the multiple angles to obtain the contrast-enhanced image data by compounding the multiple weighted images.

9. An image enhancement method for contrast enhanced ultrasound imaging, comprising:
transmitting ultrasound waves to a region of interest containing contrast agents;
receiving echoes of the ultrasound waves to obtain echo signals;
extracting contrast-enhanced channel data according to the echo signals, wherein multiple pieces of the contrast-enhanced channel data corresponding to one time point are received through multiple receiving elements of an ultrasound probe to obtain contrast-enhanced channel data corresponding to the time point;
calculating an image enhancement coefficient according to the contrast-enhanced channel data corresponding to the time point;
obtaining beam-formed data according to the contrast-enhanced channel data corresponding to the time point; and
adjusting the beam-formed data according to the image enhancement coefficient to obtain contrast-enhanced image data.

10. The method of claim 9, wherein adjusting the beam-formed data according to the image enhancement coefficient comprises: multiplying the beam-formed data by the image enhancement coefficient.

11. The method of claim 9, wherein the image enhancement coefficient is indicative of correlations among multiple pieces of the contrast-enhanced channel data corresponding to the multiple receiving elements of the ultrasound probe.

12. The method of claim 9, wherein calculating the image enhancement coefficient corresponding to the time point according to the contrast-enhanced channel data corresponding to the time point comprises:
performing an envelope detection on each piece of the contrast-enhanced channel data corresponding to the time point to obtain envelope data, and calculating the correlation between each piece of the contrast-enhanced channel data corresponding to the time point according to the envelope data, wherein the envelope detection comprises an envelope detection at a power; or
calculating the correlation between each piece of the contrast-enhanced channel data corresponding to the time point directly using the contrast-enhanced channel data corresponding to the time point; or
performing a phase detection on each piece of the contrast-enhanced channel data corresponding to the time point to obtain phase data, and calculating the correlation between each piece of the contrast-enhanced channel data corresponding to the time point according to the phase data; or
performing a Fourier transform on each piece of the contrast-enhanced channel data corresponding to the time point to obtain frequency domain data, and calculating the correlation between each piece of the contrast-enhanced channel data corresponding to the time point according to the frequency domain data.

13. The method of claim 9, wherein,
transmitting the ultrasound waves to the region of interest containing the contrast agents, receiving the echoes of the ultrasound waves to obtain the echo signals and extracting the contrast-enhanced channel data according to the echo signals comprises:
transmitting ultrasound waves in multiple angles to the region of interest containing the contrast agents;
receiving echoes of the ultrasound waves in the multiple angles to obtain echo signals corresponding to the multiple angles; and
extracting contrast-enhanced channel data corresponding to each angle of the multiple angles according to echo signals corresponding to the angle; and
calculating the image enhancement coefficient according to the contrast-enhanced channel data corresponding to the time point, obtaining the beam-formed data according to the contrast-enhanced channel data corresponding to the time point and adjusting the beam-formed data according to the image enhancement coefficient to obtain the contrast-enhanced image data at the time point comprises:
calculating image enhancement coefficient and beam-formed data corresponding to each angle of the multiple angles according to contrast-enhanced channel data corresponding to the angle; and
adjusting the beam-formed data corresponding to each angle according to the image enhancement coefficient corresponding to the angle to obtain a piece of adjusted data corresponding to the angle, and obtaining multiple pieces of the adjusted data corresponding to the multiple angles according to contrast-enhanced channel data corresponding to the multiple angles; and
the method further comprises performing coherent compound processing on the adjusted data corresponding to the multiple angles to obtain contrast-enhanced image data corresponding to the multiple angles by compounding the multiple pieces of the adjusted data corresponding to the multiple angles.

14. An image enhancement method for contrast enhanced ultrasound imaging, comprising:
transmitting ultrasound waves to a region of interest containing contrast agents;
receiving echoes of the ultrasound wave to obtain echo signals;
extracting contrast-enhanced channel data according to the echo signals, wherein multiple pieces of the contrast-enhanced channel data corresponding to one time point are received through multiple receiving elements of an ultrasound probe to obtain contrast-enhanced channel data corresponding to the time point;
calculating an image enhancement coefficient according to the contrast-enhanced channel data corresponding to the time point;
performing weighting processing on the calculated image enhancement coefficient and the contrast-enhanced channel data corresponding to the time point to obtain weighted channel data;
performing beam-forming on the weighted channel data to obtain beam-formed data; and
obtaining contrast-enhanced image data corresponding to the time point according to the beam-formed data.

15. The method of claim 14, wherein the image enhancement coefficient is obtained by calculating correlations among the multiple pieces of the contrast-enhanced channel data corresponding to a same location point or the same one time point.

16. The method of claim 14, wherein the contrast-enhanced channel data is obtained by one of:
- performing time-delay processing on the echo signals, and extracting the contrast-enhanced channel data according to the processed echo signals; or
- extracting the contrast-enhanced channel data, and performing time-delay processing on the extracted contrast-enhanced channel data.

17. The method of claim 14, wherein,
transmitting the ultrasound waves to the region of interest containing the contrast agents, receiving the echoes of the ultrasound waves to obtain the echo signals and extracting the contrast-enhanced channel data according to the echo signals comprises:
- transmitting ultrasound waves in multiple angles to the region of interest containing the contrast agents;
- receiving echoes of the ultrasound waves in the multiple angles to obtain echo signals corresponding to the multiple angles; and
- extracting contrast-enhanced channel data corresponding to each angle of the multiple angles according to echo signals corresponding to the angle to obtain contrast-enhanced channel data corresponding to the multiple angles;

calculating the image enhancement coefficient according to the contrast-enhanced channel data corresponding to the time point, performing the weighting processing on the calculated image enhancement coefficient and the contrast-enhanced channel data corresponding to the time point to obtain the weighted channel data and performing the beam-forming on the weighted channel data to obtain the beam-formed data comprises:
- calculating image enhancement coefficient corresponding to each angle of the multiple angles according to contrast-enhanced channel data corresponding to the angle;
- performing the weighting processing on the image enhancement coefficient corresponding to each angle and the contrast-enhanced channel data corresponding to the angle to obtain weighted channel data corresponding to the angle; and
- performing the beam-forming on the weighted channel data to obtain a piece of beam-formed data corresponding to each angle to obtain multiple pieces of the beam-formed data corresponding to the multiple angles; and obtaining the contrast-enhanced image data corresponding to the time point according to the beam-formed data comprises:
- performing coherent compound processing on the beam-formed data corresponding to the multiple angles to obtain contrast-enhanced image data corresponding to the multiple angles by compounding the multiple pieces of the beam-formed data corresponding to the multiple angles.

* * * * *

UNITED STATES PATENT AND TRADEMARK OFFICE
CERTIFICATE OF CORRECTION

| | |
|---|---|
| PATENT NO. | : 11,737,734 B2 |
| APPLICATION NO. | : 16/849958 |
| DATED | : August 29, 2023 |
| INVENTOR(S) | : Xirui Zhang et al. |

It is certified that error appears in the above-identified patent and that said Letters Patent is hereby corrected as shown below:

In the Claims

Claim 1, Column 21, Line 41: "channel to obtain a beam-formed data at the one" should read --channel data to obtain a beam-formed data at the one--

Claim 8, Column 23, Line 5: "compound processing on the multiple image data corresponding" should read --compound processing on the multiple weighted images corresponding--

Signed and Sealed this
Fifteenth Day of October, 2024

Katherine Kelly Vidal
*Director of the United States Patent and Trademark Office*